United States Patent [19]

Leonard

[11] Patent Number: 4,892,734

[45] Date of Patent: Jan. 9, 1990

[54] DISPENSING PASTE FOR FORMING MEDICINAL PELLETS

[75] Inventor: Robert J. Leonard, Lynnfield, Mass.

[73] Assignee: Endocon, Inc., Boston, Mass.

[21] Appl. No.: 175,540

[22] Filed: Mar. 31, 1988

Related U.S. Application Data

[63] Continuation-in-part of Ser. No. 35,379, Apr. 6, 1987, Pat. No. 4,748,024.

[51] Int. Cl.$^4$ ............................................. A61F 13/00
[52] U.S. Cl. .................................... 424/422; 424/457; 424/489; 424/502; 415/2; 415/170; 415/178
[58] Field of Search ............... 424/489, 502, 422, 457; 514/178, 2, 170

[56] References Cited

U.S. PATENT DOCUMENTS

| | | | |
|---|---|---|---|
| 4,244,949 | 1/1981 | Gupta | 514/178 |
| 4,349,530 | 9/1982 | Royer | 424/491 X |
| 4,432,964 | 2/1984 | Shell et al. | 514/912 X |
| 4,451,460 | 5/1984 | Hansen et al. | 514/178 X |
| 4,748,024 | 5/1988 | Leonard | 424/489 |

*Primary Examiner*—Michael Lusignan

[57] ABSTRACT

A process for aliquotting precise amounts of an active ingredient and a carrier for forming pellets is provided. The active ingredient and carrier are dispensed separately and then are mixed together. The mixture is combined with a liquid to form a paste. A precise amount of the paste is dispensed and the liquid is evaporated out of the paste leaving a dry, homogeneous mixture. The dry mixture then is formed into a pellet containing the active ingredient and the carrier in precise relative amounts.

19 Claims, No Drawings

DISPENSING PASTE FOR FORMING MEDICINAL PELLETS

RELATED APPLICATION

This application is a continuation-in-part of U.S. patent application Ser. No. 07/035,379, filed Apr. 6, 1987, now U.S. Pat. No. 4,748,024, patented May 31, 1988.

BACKGROUND OF THE INVENTION

This invention relates in general to a process for making medicinal pellets and in particular to a process for dispensing precise amounts of an active ingredient and carrier.

It has become widely acknowledged that standard oral and parenteral (intravenous or intramuscular) forms of drug delivery represent relatively inefficient means of administering therapeutic pharmaceuticals, due to considerable drawbacks associated with conventional drug-delivery methods. These drawbacks arise from the way in which standard dosage forms of pharmacologically active compounds are absorbed into the body, circulated through the blood stream, cleared and excreted. Conventional routes of administration generally require the administration of far more of a drug than is therapeutically warranted so that there will be adequate blood levels of drug between doses ("spiking"). Moreover, there are many therapeutically vital substances which present a narrow ratio of efficacy to toxicity that do not, therefore, lend themselves to traditional routes of administration. Additionally, drugs that require daily compliance with a multiple-dose regimen on the part of the patient pose a major problem in the management of the chronically ill, elderly, those with emotional disorders, and people whose lifestyles do not comfortably accommodate regular routine. The lists of conditions requiring such regimens is extensive and includes: diabetes; psychiatric diseases; cancer; and coronary artery disease, to name only a few.

In recent years, various types of novel sustained release drug-delivery systems have begun to receive widespread attention. Such drug-delivery systems include certain implantable devices which slowly dissolve or somehow release drugs while under the patient's skin. Implants are particularly effective and economical forms of treatment because a single administration of such a product can deliver, over a long period of time (a year or more), adequate therapeutic serum levels of a drug without reliance on patient compliance, frequent clinic visits and while avoiding over medication due to "spiking".

Of the known implantable drug delivery systems, bioabsorbable implants are preferred because such implants do not require surgical removal when the drug is depleted. Bioabsorbable implants can be made by various methods and utilizing various materials. Several methods have been practiced with steroid drugs. For example, a bioabsorbable implant can be made by tightly compressing a combination of a nonactive biocompatible binder and the steroid into a pellet. Such a pellet releases steroid more slowly and more uniformly than a pellet containing only pure steroid. The rate of release and the uniformity of release depend both on the precise relative amounts of the steroid and binder and on the homogeneity of the mixture prior to compression.

An important improvement over the compression process for making pellets, which results in even longer and more constant dissolution rates, is a method of melting a drug together with a sufficient amount of a nonactive lipoid carrier resulting, when cooled, in a "fused" pellet. Such fused pellets are capable of delivering microgram quantities of drug daily for a year or more. It is important that these pellets contain a homogeneous mixture of active ingredient and carrier in precise relative amounts to insure predictable and desirable release kinetics. This is particularly true where drugs such as steroids are being delivered because anything but a precise dosage could be ineffective or even harmful to the patient.

Fused pellets have proven unsuitable for a variety of reasons, largely related to the manufacturing processes used which are not easily reproducible. The background of such fused implants is discussed in greater detail in U.S. Pat. No. 4,244,949 (Gupta).

The methods suggested by Gupta and others for making such a fused implant rely heavily upon manual skills and do not lend themselves to automated mass production techniques. In particular, the best of the prior art methods requires pre-measuring and dispensing into very small vessels precise, minute amounts of active ingredient and carrier. Pre-measuring and dispensing of the ingredients by hand into the vessels introduces the potential for error and contamination. Moreover, this practice may necessitate an undesirable degree of human exposure to certain drugs in powder form, demanding the strictest controls according to the rules promulgated by the FDA. There currently are no acceptable substitutes for hand dispensing because it is believed that standard pharmaceutical dispensing machinery does not dispense the very small quantities of powder required for making such fused pellets with sufficient accuracy. This is especially true when the active ingredient comprises over 50% of the total pellet volume.

This invention overcomes these and other shortcomings. A process is provided for dispensing starting materials and forming a pellet that does not require the human manipulation and judgment previously enumerated and that is capable of automation and suitable for large-scale commercial production.

A particular object of the invention is to provide a process for dispensing an intimate mixture of starting materials in precise relative amounts and in an automated fashion where the active ingredient comprises over 50% of the final drug product.

SUMMARY OF THE INVENTION

A process for aliquotting precise amounts of an active ingredient and a carrier for forming pellets is provided. The active ingredient and carrier are dispensed separately and then are mixed together. The mixture is combined with a liquid to form a paste. The paste is dispensed and the liquid is evaporated out of the paste leaving a dry, homogeneous mixture. The dry mixture then is formed into a pellet containing the active ingredient and the carrier in precise relative amounts.

The paste may be dispensed into conventional pellet-forming chambers or into very small, specialized chambers, such as a fluorocarbon tube having a very small inner diameter (i.d.). The paste also may be dispensed as a bead of material or may be applied as a thin skin of material. The paste is dispensed preferably from a syringe, a micropipette or an automated device.

The paste is particularly useful for dispensing homogeneous mixtures of very small quantities of drugs and carriers. It is particularly well suited to deliver quantities of a steroid drug or a peptide drug and a lipoid carrier, the drug being present in an amount of at least 40% of the total weight of the drug and carrier. Suitable liquids for forming the paste include ethyl alcohol and diethylether.

In one significant case, the paste is made of an antifertility steroid molecule such as norethindrone, a lipoid carrier such as pure cholesterol and a volatile liquid such as ethyl alcohol or diethylether. In another significant case, the paste is made of a requlatory peptide such as growth hormone-releasing hormone, a lipoid carrier such as cholesterol acetate and a volatile liquid such as ethyl alcohol or diethylether. Other applications may include a variety of other drugs, carriers and liquids.

DETAILED DESCRIPTION OF THE PREFERRED EMBODIMENT

The accurate dispensing of the starting materials for forming a medicinal implant is achieved by forming a paste made from the powdered mixture of starting materials and a liquid such as ethyl alcohol or diethylether, which liquid may be dried out of the starting materials after dispensing, utilizing, for example, a standard vacuum oven. By forming a paste, the material can be dispensed accurately from a standard, automated device such as a micropipetter. The paste may be manufactured to have the flow characteristics of ordinary toothpaste or molasses, as desired. By forming a paste, the precise relative amounts of steroid and carrier are maintained homogeneously throughout the paste and individual manual measurements are thus obviated.

The liquid agents used to formulate the paste may be ethyl alcohol, diethylether or any volatile organic solvent which can be evaporated completely and which when combined with the starting materials yield suitable flow characteristics. The liquid agent should be of a nature that promotes quick drying. The liquid agent, of course, should not be of a nature which affects the activity of the active ingredient.

The invention may be used in the formation of a fused pellet containing an active steroid drug and cholesterol in precise relative amounts, and particularly those containing at least 50% steroid drug. The process for making such a fused pellet is described in related U.S. patent application Ser. No. 07/035,379, the disclosure of which is incorporated herein by reference. The preferred embodiment of the process disclosed in that application required the formation of a thin skin of starting materials on a heat conductive surface. The formation of the thin skin presented several technical problems. These problems were overcome using the paste of this invention. The paste simply may be spread onto the heat conductive surface. The volatile liquid then is evaporated out of the paste leaving a thin skin of a homogenous mixture of the starting materials in precise amounts.

The paste also may be used to dispense accurate relative amounts of a peptide and a carrier for forming compressed pellets in very small chambers. Such pellets may be formed, for example, in very small fluorocarbon tubes having an i.d. of 2.4 mm. Premeasuring and dispensing the starting materials by hand into such small tubes to result in a homogeneous mixture of the starting materials present in precise relative amounts is problematic Using the paste of this invention overcomes these problems. The paste may be introduced by a micropipette into the tube. The tube is then placed in a vacuum oven and the liquid is evaporated out of the mixture leaving a homogeneous mixture of the carrier and the peptide in the fluorocarbon tube. A pellet may be formed in this chamber according to various techniques.

It should be understood that various changes and modifications of the embodiments described may be made within the scope of this invention. Only two active ingredients, norethindrone and growth hormine-releasing hormone, are described in the following examples. Other active ingredients of course are contemplated. In particular, the paste provides a method for delivering very small quantities of a homogeneous mixture of virtually any drug and any carrier in precise relative amounts, especially when the active ingredient is present in amounts of more than 5% by weight of the mixture of starting materials.

When steroids are the drug of choice, other steroids include, but by no means are limited to, aldosterone, androstane, androstene, androstenedione, androsterone, cholecalciferol, cholestane, cholic acid, corticosterone, cortisol, cortisol acetate, cortisone, cortisone acetate, deoxycorticosterone, digitoxigenin, ergocalciferol, ergosterol, estradiol, 17-$\alpha$, estradiol-17$\beta$, estriol, estrane, estrone, hydrocortisone, lanosterol, lithocholic acid, mestranol, $\beta$-methasone, norethindrone, piednisolone, pregnane, pregnenolone, progesterone, spironolactone, testosterone, triamcinolone and their derivatives.

When peptides are the drug of choice, other peptides include, but by no means are limited to growth hormone factors, growth hormone and growth hormone-releasing hormone, gonadotropin-releasing hormone, and its agonist and antagonist analogues, somatostatin and its analogues, gonadotropins such as luteinizing hormone and follicle-stimulating hormone, peptide T, thyrocalcitonin, parathyroid hormone, glucagon, vasopressin, oxytocin, alpha and beta melanocyte-stimulating hormones, peptide molecules which stimulate erythrocyte, leucocyte and immunocyte growth and function such as colony stimulating factors (CFS 1 and 2), erythropoietin and lymphokines (including interleukin I and II), angiotensin I and II, bradykinin, kallidin, adrenocorticotropic hormone, thyroid stimulating hormone, insulin, glucagon and the numerous analogues and congeners of the foregoing peptides.

Only two carriers, cholesterol and cholesterol acetate, are described. However, other carriers, binders, excipients and emulsifiers well known to those skilled in the art may be added or substituted as starting materials. For example, cholesterol derivatives, including cholesteric esters such as cholesterol chloride, may be used. Sterol carriers other than cholesterol may be used. Non-sterol carriers include, but by no means are limited to, fatty acids and neutral fats. Thus, it is intended that all matter contained in the above-description or described in the following examples shall be interpreted in an illustrative and not limiting sense.

EXAMPLE 1

85 grams of pharmaceutical grade, micronized norethindrone (provided by Diosynth, Inc. of Chicago, Ill.) and 15 grams of pure, pharmaceutical grade cholesterol (provided by ICN Pharmaceuticals of Covina, Calif.) were intimately mixed and ground in a mortar and pestle. Two grams of the mixture of norethindrone and cholesterol were mixed with 2 ml of 100% laboratory grade ethyl alcohol using a spatula to form a paste. The paste was spread onto the spatula in a thickness of about 0.5 mm and allowed to dry in a vacuum oven for 30 minutes at 60° C. The stainless steel spatula was approximately 20 mm in length and 10 mm in width and was covered uniformly with a fine layer of Teflon ® tape. The nonTeflon ®coated side of the spatula then was brought in contact with a hot plate which was heated to approximately 500° F. A clear melt resulted which beaded up like mercury and rolled off the surface of the spatula when the spatula was held at an angle about 45° to horizontal. The spatula was contacted with hot plate for less than 10 seconds. Upon cooling, the fused material was white, implying the lack of degradation products. There was no de-ethynylation of the norethindrone. The pellet was resilient and could be filed and formed with a very gentle abrasive action. Based on a visual light microscopy of the fracture surface, the pellet appeared to have the same characteristics of the very best of those made according to the prior art methods.

EXAMPLE 2

Pharmaceutical grade, micronized norethindrone (obtained from Diosynth, Inc. of Chicago, Ill.) and pure pharmaceutical grade cholesterol (obtained from ICN Pharmaceuticals of Covina, Calif.) were combined at a ratio of 85:15% by weight, respectively, intimately mixed and ground in a mortar and pestle. Between 40 and 50 grams of this mixture were weighed into individual vials. Between 5 and 1.0 ml of diethylether was combined with the mixture using a Pasteur pipette to form a slurry This slurry was immediately transferred by the Pasteur pipette to a melt cup having a non-stick surface substantially as described in U. S. patent application Ser. No. 07/035,379. One ml of the flowable slurry was applied, being spread across the non-stick surface as a skin. The diethylether was allowed to evaporate out of the slurry, the evaporation being assisted by placing the melt cup in a vacuum oven. Once the paste had dried, the melt cup was subjected to conditions as described in U. S. patent application Ser. No. 07/035,379 to form a flash-flow fused pellet.

EXAMPLE 3

A carrier, such as powdered cholesterol acetate obtained from Sigma Chemical Co. of St. Louis, Mo., and a peptide, such as growth hormone-releasing hormone obtained from Bisendorf Peptides of Grosburgwedel, German Bundes Republik, are combined in approximate proportions of 60% cholesterol acetate and 40% growth hormone-releasing hormone by weight. Diethylether is added to this mixture in an amount sufficient to form a ductile paste. This paste then is dispensed in a precise quantity using a micropipette into an open-ended fluorocarbon tube having an inner diameter of 2.4 mm. The fluorocarbon tube is placed in a vacuum oven to evaporate out the diethylether leaving a homogeneous mixture of the starting materials in precise relative amounts. The dried mixture then is formed into a pellet by plugging one end of the fluorocarbon tube and compressing the dry mixture against a plug with a compression pin introduced into the opposite end of the fluorocarbon tube.

What is claimed is:

1. A process for dispensing an active ingredient and a carrier for forming pellets containing said active ingredient and said carrier comprising, forming a paste from said active ingredient, said carrier and a liquid,
dispensing said paste,
causing said liquid to be evaporated out of said paste, leaving a dry mixture, and
forming a pellet from said dry mixture.

2. A process for dispensing an active ingredient and a carrier for forming pellets containing said active ingredient and said carrier, comprising,
dispensing a first amount of said active ingredient,
dispensing a second amount of said carrier,
mixing said first and second amounts together with a liquid to form a paste,
dispensing said paste,
causing said liquid to be evaporated out of said paste leaving a dry mixture of said active ingredient and said carrier, and
forming a pellet from said dry mixture.

3. A process as claimed in claim 2 wherein said active ingredient and said carrier are dispensed in relative amounts such that said active ingredient comprises at least 40% of the total amount of the active ingredient and carrier dispensed.

4. A process as claimed in claim 2 wherein said active ingredient and said carrier are mixed with a liquid that is a volatile organic solvent.

5. A process as claimed in claim 3 wherein said active ingredient is a steroid drug and wherein said steroid and said carrier are mixed with said liquid to form said paste.

6. A process as claimed in claim 3 wherein said active ingredient is a peptide drug and said peptide drug and said carrier are mixed with said liquid to form said paste.

7. A process as claimed in claim 3 wherein said carrier is selected from the group consisting of cholesterol, derivatives of cholesterol, cholesteric esters and derivatives of cholesteric esters and wherein said active ingredient and at least one carrier from said group are mixed with said liquid to form said paste.

8. A process as claimed in claim 7 wherein said active ingredient is selected from the group consisting of steroid drugs and peptide drugs and wherein said drug and said carrier are mixed with said liquid to form said paste.

9. A process as claimed in claim 1 wherein said active ingredient is norethindrone and said carrier is cholesterol and wherein said norethindrone and said cholesterol are mixed with said liquid to form said paste.

10. A process as claimed in claim 8 wherein said drug and said carrier are mixed with a liquid selected from the group consisting of alcohols and ethers.

11. A flowable, paste useful for dispensing an active ingredient and a carrier in precise relative amounts to form a medicinal pellet, said paste containing an effective portion of a drug as the active ingredient and a carrier, the drug and carrier homogeneously dispersed in a transitory, volatile liquid.

12. A flowable paste as claimed in claim 11 wherein said carrier is present in an amount by weight of at least 15% relative to the amount of the drug, exclusive of the weight of the volatile liquid.

13. A flowable paste as claimed in claim 11 wherein said drug is present in an amount by weight of at least 40%, exclusive of the weight of the solvent.

14. A flowable paste as claimed in claim 11 wherein said carrier is selected from the group consisting of,
sterols,
cholesterol,
cholesterol acetate,
cholesterol chloride, cholesteric esters, and
derivatives of cholesterol and cholesteric esters.

15. A flowable paste as claimed in claim 11 wherein said drug is selected from the group consisting of steroid drugs and peptide drugs.

16. A flowable paste as claimed in claim 13 wherein said drug is selected from the group consisting of steroid drugs and peptide drugs.

17. A flowable paste as claimed in claim 14 wherein said drug is selected from the group consisting of steroid drugs and peptide drugs.

18. A flowable paste as claimed in claim 17 wherein said liquid is an alcohol or an ether.

19. A flowable paste as claimed in claim 17 wherein the drug is norethindrone or growth-hormone releasing hormone.

* * * * *